(12) United States Patent
Campbell

(10) Patent No.: US 6,244,866 B1
(45) Date of Patent: Jun. 12, 2001

(54) TONGUE SUPPRESSING BITE BLOCK

(76) Inventor: Regina Campbell, 1054 W. 2525 North, Layton, UT (US) 84041

( * ) Notice: Subject to any disclaimer, the term of this patent is extended or adjusted under 35 U.S.C. 154(b) by 0 days.

(21) Appl. No.: 09/474,309

(22) Filed: Dec. 29, 1999

(51) Int. Cl.[7] .................................................. A61C 5/00
(52) U.S. Cl. ............................ 433/140; 433/93; 600/238
(58) Field of Search .................................... 433/140, 138, 433/93, 136; 600/237, 238

(56) References Cited

U.S. PATENT DOCUMENTS

| 2,220,674 | * | 11/1940 | Bloomheart | 600/238 |
|---|---|---|---|---|
| 3,924,333 | | 12/1975 | Erickson | 32/33 |
| 4,053,984 | | 10/1977 | Moss | 32/33 |
| 4,167,814 | | 9/1979 | Schubert | 32/33 |
| 5,340,313 | | 8/1994 | Hussin | 433/136 |
| 5,588,836 | | 12/1996 | Landis et al. | 433/93 |
| 5,590,643 | * | 1/1997 | Flam | 128/200.26 |
| 5,735,691 | * | 4/1998 | Fetter | 433/140 |
| 5,890,899 | | 4/1999 | Sclafani | 433/140 |

* cited by examiner

Primary Examiner—John J. Wilson
Assistant Examiner—Melba Bumgarner
(74) Attorney, Agent, or Firm—Pate Pierce & Baird

(57) ABSTRACT

A dental apparatus for maintaining the mouth of a patient in an open position during a dental procedure. The apparatus having a bite block that is inserted into the patient's mouth between the upper and lower molars on either side of a patient's mouth. Disposed in operable relation to the bite block is a tongue suppressor for retaining the tongue of a patient in the bottom cavity of the mouth. The tongue suppressor having a retaining arm that extends across the tongue away from the bite block. Opposite the bite block on the retaining arm is a flange that extends downward toward the bottom of the mouth. The retaining arm and the flange retain the patient's tongue in the bottom cavity of the patient's mouth.

22 Claims, 3 Drawing Sheets

TONGUE SUPPRESSING BITE BLOCK

BACKGROUND

1. The Field of the Invention

The present invention relates to dental implements and, more particularly, to novel apparatus for maintaining the mouth of a patient in an open position and retaining the tongue.

2. The Background Art

When a dentist performs a procedure, the patient's mouth must be held open for access to the teeth. In simple, short procedures, such as an examination or teeth cleaning, the patient may be able to open his mouth wide and long enough for the dentist to perform the dental procedure. However, in longer and more complex procedures, the patient may tire from holding his mouth open or, in the alternative, be unable to hold his mouth open due to the pain of the dental procedure or numbness resulting from the anesthesia. In these types of procedures, dental mouth props may be used by a dentist in an effort to mechanically maintain the patient's mouth in the open position.

As appreciated by those skilled in the art, dental mouth props may function in a variety of ways. For example, some prior art dental mouth props incorporate a tubular frame inserted between the cheek and gum of a patient's mouth. Dental mouth props of this general nature generally mask the outer surface of the teeth, thereby making it difficult to view, drill, fill and/or perform other dental procedures on the teeth. Moreover, the dental mouth prop is usually positioned on both sides of the mouth, thus having the effect of obscuring the dentist's view and access from all angles within the patient's mouth.

Other dental mouth props have been developed by those skilled in the art which engage the teeth of a patent. These prior art dental mouth props are typically inserted between the upper and lower molars on one side of the mouth allowing a dentist to view and have working access to a larger area of the patient's mouth. However, these devices have no provisions for patient comfort and may cut and irritate the patient's mouth, gums and cheeks. Often these types of dental mouth prop devices are small and could be accidentally swallowed by a patient causing severe injury to the patient.

As appreciated by those skilled in the art, a patient's tongue may also interfere with a dental procedure by interfering with the dentist's visibility and by interrupting the limited available work space within the patient's mouth. Traditionally, dentists have used a variety of implements in an effort to suppress the tongue during a dental procedure. For example, dentists have used hand-held suppressors to hold the tongue in place. However, the use of hand-held tongue suppressors restricts the dentist to the use of only one hand or requires a dental assistant to hold the suppressor in place. Hand-held suppressors can therefore crowd the available working space within the mouth and prevent a clear view of the targeted work area.

Currently available dental mouth props which cooperate with other dental-type tools are usually expensive and necessitate reuse to recover the cost of the device. In order for a dental device to be reused, it must be sterilized to obviate contamination and thereby reduce the risk of infecting a subsequent patient. As appreciated by those skilled in the art, the process of sterilization adds to the overall cost of a dental procedure, such cost being typically passed on to the patient. The sterilization processes that are typically used in a dental office generally depend upon the specific characteristics or properties of the tools or dental implements being sterilized. For example, during beat or steam sterilization, many prior art dental mouth props that are formed of polymers or a polymeric materials would tend to melt or become seriously distorted at the high temperatures and pressures required by autoclaving or using a steam sterilization process. Accordingly, such prior art dental mouth props must be sterilized using conventional chemical methods after implementing an ultrasonic cleaning. A significant disadvantage with chemically sterilizing prior art polymeric dental mouth props is that the chemicals commonly used for chemical sterilization often leave an unpleasant tasting residue on dental mouth prop, which ultimately adds to a patient's discomfort as a result of the distaste.

Incorporating operable features to prior art dental mouth props can make it difficult to work around in an already restricted work area within the mouth of a patient. For example, dental mouth props having integrated irrigation and aspiration systems may include tubes and appendages that extend outside of the oral cavity, thereby giving the dentist or oral surgeon less space to work in. Moreover, many patients are already apprehensive about having to go to the dentist, much less having to accommodate a dental prop having one or more large, uncomfortable appendages stuffed into their mouths.

Another significant disadvantage with prior art dental mouth props having operable appendages is that they are generally bulky and cumbersome when disposed within the patient's mouth. As appreciated, during a dental procedure, the mouth of a patient is often crowded with the hands of the dentist and one or more assistants, together with suction, aspiration, a drill, a polisher, a curing light and/or other dental instruments. In this regard, when a dental mouth prop has additional structural features and bulky appendages, the mouth of the patient becomes more crowded and less accessible to the dentist for conducting the procedure.

While prior art dental mouth prop devices may appear generally suitable for their intended purposes, these prior art dental mouth props nevertheless leave much to be desired from the standpoint of effectiveness of operation, manufacturing costs, simplicity of construction in relation to a multiplicity of parts and functionality as to universal application. As will be appreciated in this particular art, economic considerations are significant when dealing with the highly competitive dental industry, since complicated devices are frequently found to be commercially impractical. Accordingly, even a slight savings in cost may substantially enhance the commercial appeal of a particular dental implement or assembly when considering issues of mass production of the product.

A need further exists for a dental apparatus which supportably maintains the mouth of a patient in an open position while retaining the tongue within the bottom cavity of the mouth (e.g., the mandibular arch). It would also be an improvement in the art if such a dental apparatus were inexpensive to manufacture and disposable, thereby eliminating the risks and costs associated with sterilization and potential contaminated reuse. It would be a further advancement in the art if the device were equipped with a safety feature that would prevent accidental swallowing. A need also exists for a mouth prop and tongue suppressor that fits within the oral cavity with no bulky or cumbersome appendages that interfere with the dental procedure and cause discomfort to a patient.

In accordance therewith, it would be desirable to provide a novel tongue suppressing bite block which realizes the advantages of the prior art dental mouth prop devices while at the same time eliminates the disadvantages associated therewith. Such a tongue suppressing bite block is disclosed and claimed herein.

SUMMARY AND OBJECTS OF THE INVENTION

In view of the foregoing, it is a primary object of the present invention to provide a novel tongue suppressing bite block which is capable of maintaining the mouth of a patient in an open position while retaining the patient's tongue in the lower region of the mouth to avoid obfuscating the limited available work area within the patient's mouth.

It is also an object of the present invention to provide a tongue suppressing bite block which is formed of a disposable material, thus avoiding the disadvantages and costs associated with having to clean and sterilize dental implements.

It is further an object of the present invention to provide a tongue suppressing bite block which facilitates dental procedures by improving visibility in and around the work area within a patient's mouth.

Additionally, it is an object of the present invention to provide a tongue suppressing bite block having a simple, non-bulky design that does not require structural appendages that protrude from the mouth of the patient which ultimately tend to interfere with the dentist performing the dental procedure and generally cause discomfort to the patient.

It is another object of the present invention to provide a tongue suppressing bite block having a size and shape sufficient for being introduced into either side of the patient's mouth, thereby eliminating the need for a dentist to stock various sizes (e.g., small, medium and large) in order to accommodate different dental arch configurations.

Similarly, it is a further object of the present invention is to provide a bite block having a structural configuration capable of maintaining a right engaging or left engaging tongue suppressor in adjustable engagement therewith on the respective side of the patient's mouth.

It is also an object ofthe present invention to provide a tongue suppressing bite block which minimizes patient discomfort when disposed within the patient's mouth.

It is a still further object of the present invention to provide an emergency extraction mechanism whereby a practitioner can remove the bite block and tongue suppressor in case of an emergency (ie., choking, vomiting, gagging or the like).

Consistent with the foregoing objects, and in accordance with the invention as embodied and broadly described herein, a dental apparatus for suppressing the tongue and maintaining the mouth of a patient in an open position comprises a bite block having an integrated tongue suppressor engageably disposed in relation thereto. In one currently preferred embodiment of the present invention, the bite block is made from a resilient, deformable material that allows the teeth to firmly hold the bite block in place. The tongue suppressor has a retaining arm that extends from its engagement with the bite block across the tongue. Disposed in relation to an end of the retaining arm opposite the bite block, a flange projects downward into the inferior aspect of the oral cavity (e.g., the bottom cavity of the mouth). Structurally, the flange forms a substantial right angle in relation to its disposition to the retaining arm.

The bite block may be configured with one or more shoulders that extend along the sides of the teeth. These shoulders serve to position the bite block on the teeth and to prevent lateral slippage. If shoulders are present both inside and outside of the teeth, the shoulders may be of varying heights. Because the interior shoulder may project into a target area of the dental procedure, it may be of a lesser height, thereby providing more clearance than the exterior shoulder. Additionally, the lower interior shoulders will not rub on the roof of the mouth and cause pain or discomfort to the patient.

An integrated bite block and tongue suppressor may be made from a single, unitary unit. It may be preferable, however, for the bite block and tongue suppressor to be formed as two cooperating members. In this regard, a slot may be formed in the body of the bite block which is adapted to receive and selectively retain the retaining arm of the tongue suppressor. In one presently preferred embodiment, the retention arm may slide freely into and out of the slot. In alternate embodiments, retention mechanisms such as a friction fit, a mechanical lock, and the like are incorporated in to the design of the bite block and the tongue suppressor to hold the retaining arm in the slot of the bite block.

Since the bite block will generally be held in place by the teeth of a patient, the bite block includes a surface area for engaging the teeth. In certain embodiments, the surface area may be elastically or plastically distortable, thus allowing the teeth of the patient to sightly penetrate and disform the surface area. In other presently preferred embodiments, the surface area of the bite block may be equipped with ridges, indentations, ribs and/or the like to provide means for engaging the teeth and preventing slippage.

In one presently preferred embodiment of the present invention, the bite block may be employed on either side of the mouth. The tongue suppressor may be adapted to either side of the mouth by producing a mirror image of the structural design of the tongue suppressor. In certain embodiments, the bite block may be angled to match the desired angle of an open mouth. This angle of engagement may vary depending on the age and size of a patient as well as the size of the area needed for conducting the dental procedure.

In order to prevent cutting and injury to the patient's mouth, the tongue suppressing bite block can be formed with rounded edges and surfaces. In one embodiment, the exterior surface of the bite block is curved to conform to the general shape of a patient's mouth. As will be appreciated, surfaces may be rigid, stiff or flexible, as required. Plastic reformation of material over a stiffer substrate may also be used to balance support and comfort.

In certain embodiments of the invention, the tongue suppressing bite block is formed from a material selected to be disposable. In addition, the present invention is preferably pre-sterilized and packaged. Moreover, the tongue suppressing bite block of the present invention may be infused with a selected flavoring, if desired.

As appreciated in the dental arts, during a dental procedure, fluid may begin to build up from salivation, bleeding and irrigation. In one presently preferred embodiment of the present invention, the flange section of the tongue suppressor maybe formed having an access notch where suction can be applied to eliminate fluids retained in the lower cavity of the patient's mouth.

In one presently preferred embodiment, an emergency extraction mechanism may also be incorporated into the tongue suppressing bite block to reduce the risk of a patient swallowing the apparatus during a dental procedure. In certain embodiments, an aperture may be cut or formed in the tongue suppressor or bite block. A tether, such as a length of floss or string, may then be secured in relation to the aperture such that a dentist or dental assistant can quickly pull on the tether to thereby remove the apparatus from a patient's mouth in an emergency.

As appreciated, the internal region of the mouth is a relatively small area to perform a procedure and can become crowded inside and outside by the introduction or proximity of excess dental implements. A tongue suppressing bite block in accordance with the present invention is configured to fit entirely within a patient's mouth, thereby preventing overcrowding of the work area.

The foregoing and other objects and features of the present invention will become more fully apparent from the following description and appended claims, taken in conjunction with the drawings and what may be learned by the practice of the invention as set forth hereinafter.

BRIEF DESCRIPTION OF THE DRAWINGS

The above-recited and other advantages and objects of the invention may be understood, and a more particular description of the invention briefly described above will be rendered, by reference to specific embodiments thereof, which are illustrated in the appended drawings. Understanding that these drawings depict only typical embodiments of the invention and are, therefore, not to be considered limiting of its scope, the invention will be described with additional specificity and detail through use of the accompanying drawings in which.

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 7, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
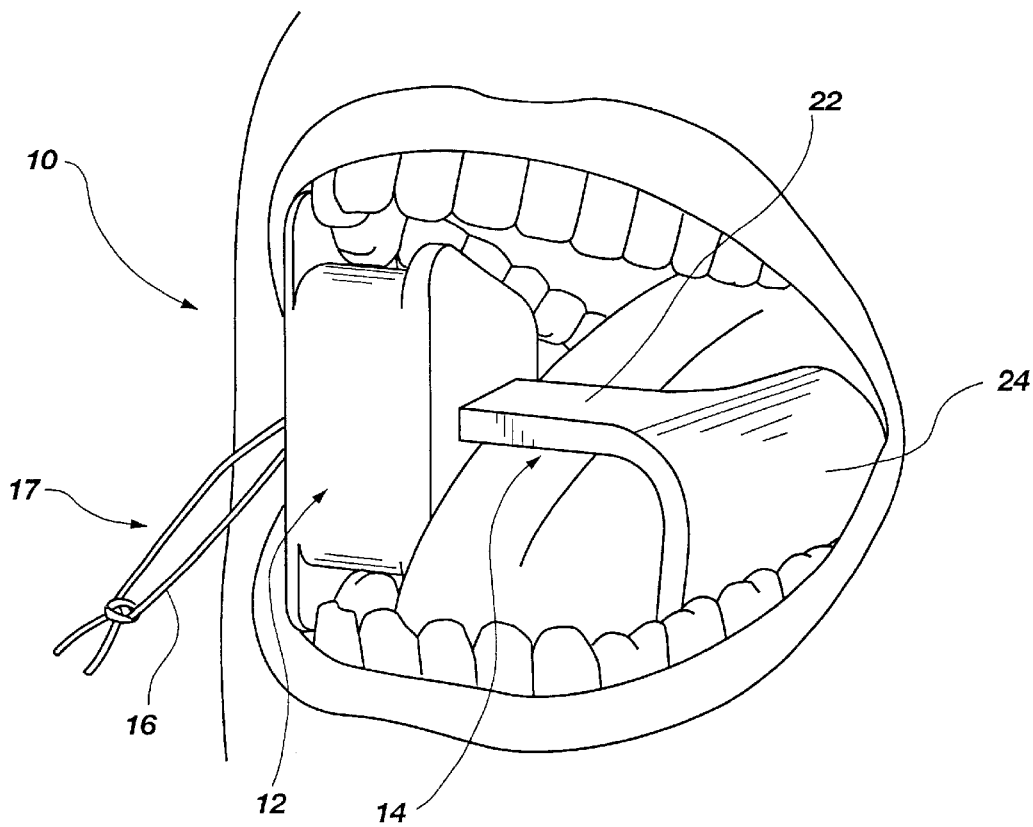
FIG. 1 is a perspective view of one presently preferred embodiment of a tongue suppressing bite block inserted into the mouth of a patient.
Figure 2:
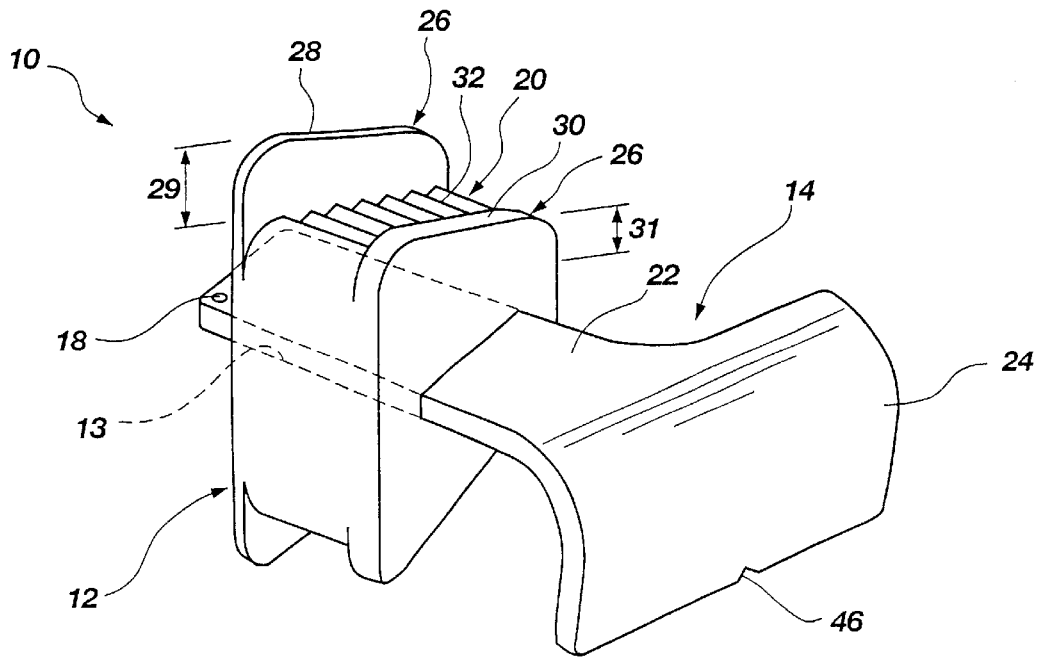
FIG. 2 is a perspective view of the embodiment illustrated in FIG. 1.

One presently preferred embodiment of the present invention, designated generally at 10, is best illustrated in FIGS. 1 and 2 and, generally, in FIGS. 1–7. As shown, a tongue suppressing bite block 10 may include a bite block 12 and a tongue suppressor 14. The tongue suppressor 14 and bite block 12 may be formed as a single unit or as two independent, but interactive members. The tongue suppressing bite block 10 may be configured to fit entirely within the mouth of a patient without protruding outwardly therefrom. In one presently preferred embodiment, the tongue suppressing bite block 10 is inserted into a patient's mouth between the upper and lower molars on either side of the mouth. In this or other embodiments of the present invention, the tongue suppressing bite block 10 may be configured to be inserted between other teeth such as the bicuspids, canines and incisors.

In one presently preferred embodiment, the components of the tongue suppressing bite block 10 maybe formed from resilient, flexible materials such as rubber, latex and other elastomeric materials. Various polymers may be selected for a combination of stiffness and flexibility as is structurally required. As the patient bites down upon the bite block 12, the teeth may sightly penetrate and/or deform both these materials, holding the apparatus 10 firmly in place. In other embodiments, all or part of the tongue suppressing bite block 10 may be made from harder or more rigid materials such as thermosets, thermoplastics, foams, other plastics or composite materials, wood, metal, ceramics, fiberglass and the like. Moreover, the components of the tongue suppressing bite block 10 may be formed by various techniques such as injection molding, blow molding, tumble molding, casting, vacuum forming and the like. The tongue suppressing bite block 10 may also be fabricated or shaped from bulk material, whether monolithic or several pieces fastened together.

In one presently preferred embodiment of the present invention, the tongue suppressing bite block 10 is formed from inexpensive materials that can easily be mass produced, such as plastics. In this manner, the tongue suppressing bite block 10 may be formed inexpensive enough to be disposable, thereby eliminating the risks associated with reuse and sterilization as well as the inherent bad taste that results from chemical sterilization. Preferably, the tongue suppressing bite block 10 of the present invention is pre-sterilized at the point of manufacture and packaged to maintain sterility until opened for use.

As appreciated by those skilled in the art, many polymers and other materials have an unusual or even unpleasant taste. Moreover, certain sterilization processes may add an unpleasant taste to the tongue suppressing bite block 10. Because the apparatus 10 is made to be inserted into a patient's mouth, it may be infused with a flavoring agent providing a taste such as bubble gum, mint, grape, cherry or the like to render the tongue suppressing bite block 10 pleasantly palatable.

As shown in the illustrated embodiments, the bite block 12 is tapered from front to back. This tapering can be selected to match the desired angle of an opened mouth. As appreciated, the angle may be varied depending on the size of the patient's mouth and the procedure-being performed. For example, if a dentist desires a large work area or access deep in the back of the mouth, the angle of the bite block 12 may be steeper to force the patient to open his mouth wider.

In one presently preferred embodiment of the present invention, the bite block 12 has an engagement surface 20 configured to engage the teeth of the patient and hold the tongue suppressing bite block 10 in place. One or more shoulders 26 may extend beyond the engagement surface 20.

The shoulders 26 may extend on either one side or opposing sides of the teeth toward the top of the mouth or the bottom of the mouth. The shoulders 26 are configured to restrict the bite block 12 from moving laterally across the teeth. An alternate embodiment of the bite block 12 of the present invention may function satisfactorily without shoulders 26. For example, with a sufficiently distortable material, the teeth may depress the engagement surface 20 of the bite block 12 with enough force to retain the tongue suppressing bite block 10 securely in place in relation to the teeth.

Preferably, the exterior shoulder 28 and the interior shoulder 30 may be formed having differing heights 29, 31, respectively. The exterior height 29 may be greater than the interior height 31 such that the interior shoulder 30 does not completely cover or shield the patient's teeth or vice versa. Functionally, the extended height 29 of the exterior shoulder 28 serves to stabilize the tongue suppressing bite block 10 and prevent lateral slippage should the teeth lose their capture on the engagement surface 20. Also, the shoulders 28, 30 may assist in gauging placement within the patient's mouth quickly.

In one presently preferred embodiment, a tongue suppressor 14 may have an elongated retention arm 22, a flange 24, or both. As best shown in FIG. 1, the elongated retention arm 22 preferably extends from either side of the bite block 12 across the patient's tongue, thereby urging the tongue into the lower cavity of the mouth (e.g., the mandibular arch region). A flange 24 may extend downward from an end of the retention arm 22 at an angle selected for comfortably holding the tongue in place.

A notch 46 may also be provided for application of an aspiration device in relation to the tongue suppressing bite block 10. Preferably, the notch 46 is formed along the bottom of the flange 24 such that when the tongue suppressing bite block 10 is inserted within the mouth of a patient, the notch 46 is located inside the teeth in the bottom cavity of the mouth. As fluids from irrigation, salivation and/or bleeding and materials such as composite and amalgam collect in the lower cavity of the mouth, aspiration may be applied relative to the notch 46 formed in the tongue suppressor 14 to remove the collected fluids and solids. The aspiration device inserted into the mouth may then be removed to avoid overcrowding of the work area during the procedure.

As best shown in FIGS. 1 and 2, an emergency extraction mechanism 17 may be provided for quick removal of the tongue suppressing bite block 10. For example, an aperture 18 may be formed in the tongue suppressor 14 or the bite block 12. A tether 16, such as a piece of floss or string, secured to the aperture 18 preferably comprises a length sufficient to allow it to extend out of the patient's mouth. The dentist or dental assistant may quickly grab the tether 16 and pull the tongue suppressing bite block 10 from the patient's mouth in case of an emergency such as panic, choking, gagging or vomiting.

Figure 3:
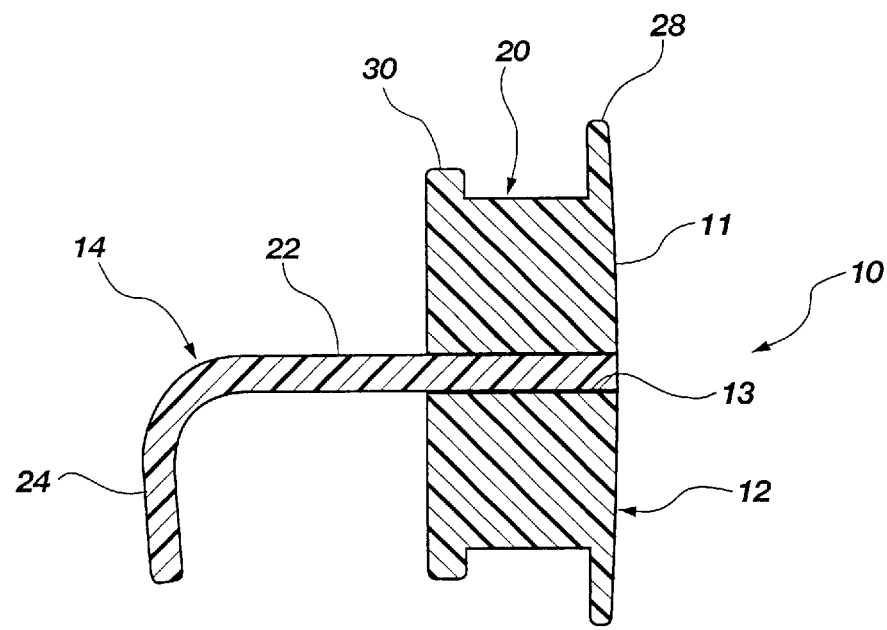
FIG. 3 is an end elevation, cross-sectional view of an alternative embodiment of an apparatus in accordance with the present invention.

Referring specifically to FIG. 3, while continuing to refer generally to FIGS. 1–7, a slot 13 is formed in the body of the bite block 12 for receiving at least a portion of the elongated retention arm 22 of the tongue suppressor 14. In one presently preferred embodiment, the tongue suppressor 14 slidably engages the slot 13 to allow an adjustment to the length of the tongue suppressor 14 in relation to the bite block 12. The slot 13 may extend through the bite block 12 such that the tether 16 attaches to the aperture 18 formed in the tongue suppressor 14. Alternatively, the slot 13 may terminate within the bite block 12 in such a manner so as to prevent the tongue suppressor 14 from extending against and irritating the cheek of a patient.

Preferably, the exterior surface 11 of the bite block 12 is configured to prevent irritation to the cheek and gums of the patient. For example, the exterior surface 11 may be rounded and shaped to conform to the rounding of the cheek thereby eliminating any irritating bulk and sharp edges.

In one presently preferred embodiment, the tongue suppressor 14 may be configured to retain the tongue from either side of the mouth. In particular, the flange 24 may be configured having an angle of engagement such that when applied against the tongue, the tongue suppressing bite block 10 retains the tongue on the left side of the bite block 12 in a patient's mouth, as best illustrated in FIG. 1. Alternatively, the flange 24 maybe configured having an angle of engagement such that when applied against the tongue, the tongue suppressing bite block 10 retains the tongue on the right side of the bite block 12 in a patient's mouth, as illustrated in FIGS. 5 and 7.

Referring now to FIGS. 4 through 7, the present invention contemplates a flange 24, 124, 224, 324 being formed having various shapes and sizes. It being appreciated that since the device of the present invention must conform to the size and shape of a patient's mouth to which it is to be introduced, it is anticipated that the various structural elements thereof can be formed in a series of different sizes and shapes to accommodate different mouth sizes and shapes.

Figure 4:
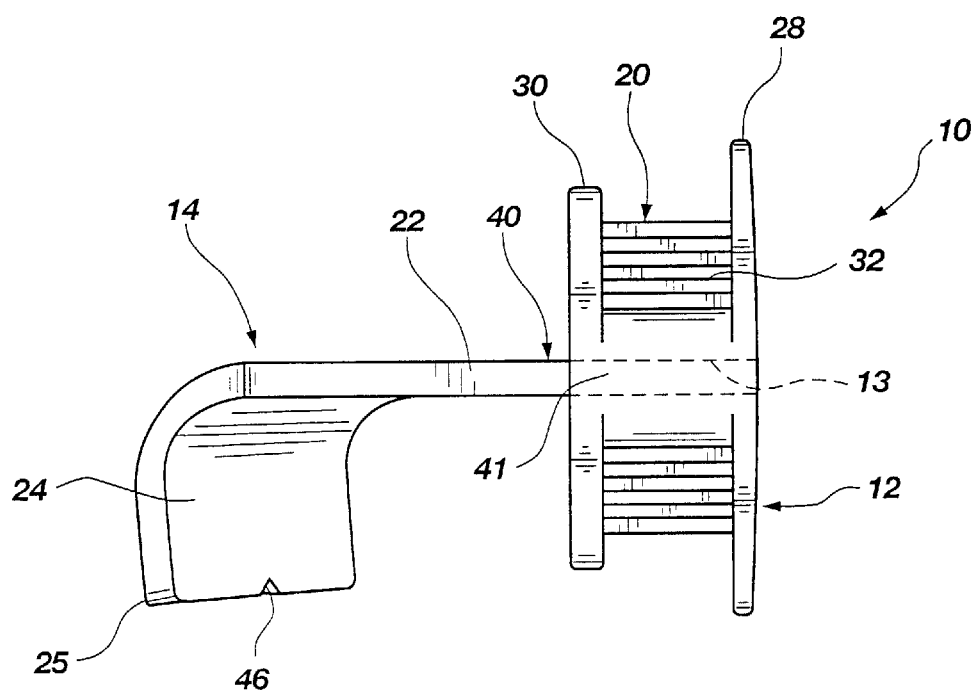
FIG. 4 is an end elevation view of the apparatus of FIG. 3 in accordance with the present invention.
Figure 5:
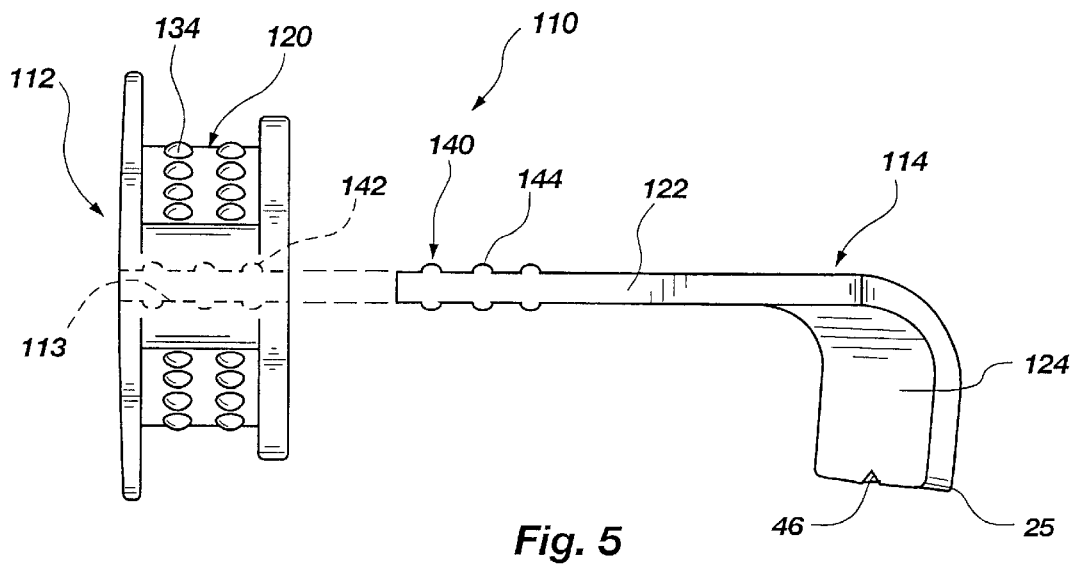
FIG. 5 is a perspective view of an alternative embodiment of an apparatus in accordance with the present invention.
Figure 6:
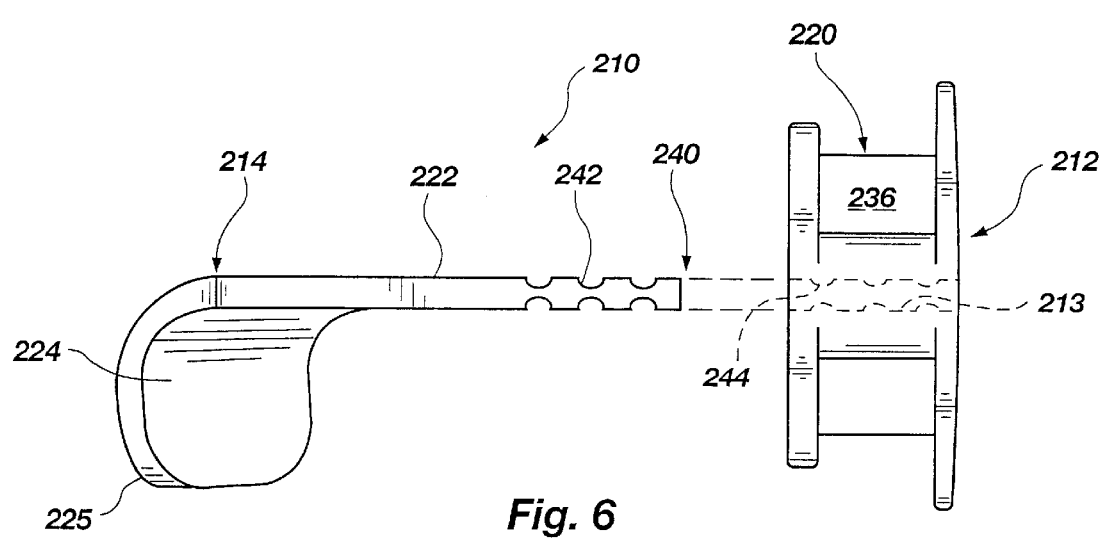
FIG. 6 is a perspective view of an alternative embodiment of an apparatus in accordance with the present invention.
Figure 7:
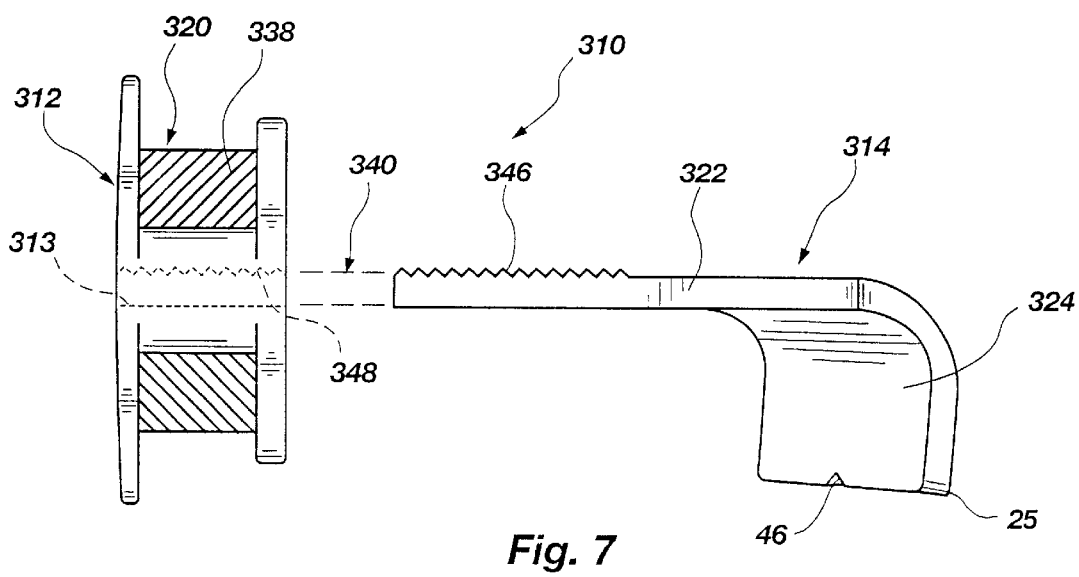
FIG. 7 is a perspective view of an alternative embodiment of an apparatus in accordance with the present invention.

For example, in the presently preferred embodiments, the flange 24, 124, 324 is formed having squared corners 25, as illustrated in FIGS. 4, 5 and 7. In an alternate preferred embodiment, the corners 225 of the flange 224 may be rounded, as illustrated in FIG. 6. In certain embodiments, the flange 24 may be substantially square and centered on the elongated retention arm 22. In other embodiments, the flange 24 may be substantially rectangular and displaced off-center, thus extending farther into the back of the mouth. In other presently preferred embodiments, the flange 224 may be rounded with or without an aspiration notch 46. Those skilled in the art will readily recognize other possible modifications and adaptations which are consistent with the spirit and scope of the present invention.

As discussed previously herein, the engagement surface 20 of the bite block 12 is adapted to firmly engage and grip against the teeth of a patient thereby urging the tongue suppressing bite block 10 to remain in place within the patient's mouth. Referring to FIG. 4, in one presently preferred embodiment of the present invention, the engagement surface 20 has a series of ridges 32 that serve to engage the contours of the teeth of a patient and hold the tongue suppressing bite block 10 in relation to its positioning in the patient's mouth. In an alternate embodiment, as shown in FIGS. 5 and 7, a plurality of ribs 134 or grooves 338, respectively, are provided along the length of the engagement surface 120, 320, respectively, of the bite block 112, 312 to provide surface texturing for engagement with the teeth. While ridges 32, ribs 134 and grooves 338 may be useful to facilitate an engagement between the bite block 12,112,338, respectively, and the patient's teeth, a smooth, malleable surface 236 may deflect elastically or plastically to engage the teeth, as illustrated in FIG. 6. It will be apparent that other surface textures of the engagement surface 20 of the bite block 12 may be provided in accordance with the inventive principles set forth herein. It is intended, therefore, that the examples provided herein be viewed as exemplary of the principles of the present invention, and not as restrictive to particular structures for implementing those principles.

In one presently preferred embodiment of the tongue suppressing bite block 10, a retention mechanism 40 is provided to retain at least a portion of the tongue suppressor 14 firmly within the slot 13 of the bite block 12. For example, as shown in FIG. 4, the slot 13 and the elongated retention arm 22 of the tongue suppressor 14 may be configured in such a manner to provide a friction fit therebetween, thus preventing the retention arm 22 from slippage unless sufficient force is applied to overcome the frictional engagement.

Referring now to FIG. 5, in an alternate preferred embodiment of the tongue suppressing bite block 110, the retention mechanism 140 may include a mechanical locking engagement between the retention arm 122 of the tongue suppressor 114 and the slot 113 formed in the bite block 112. The slot 113 may be formed with a series of indentations 142, whereas the retention arm 122 may be formed with a corresponding series of ribs 144. In operation, as the retention arm 122 is inserted into the slot 113, the ribs 144 of the retention arm 122 enter into the indentations 144 of slot 113, thereby selectively locking the bite block 112 and the tongue suppressor 114 together. Alternatively, the tongue suppressing bite block 210 may comprises ribs 244 that are formed within the slot 213 and the indentations formed along a portion of the length of the retention arm 222, as illustrated in FIG. 6.

Referring now to FIG. 7, another alternate embodiment of the tongue suppressing bite block 310 of the present invention is illustrated wherein the retention arm 322 may be formed with a series of ridges or teeth 346. Corresponding ridges 348 may be formed along the length of the slot 313. As the retention arm 322 of the tongue suppressor 314 is inserted within the internal periphery of the slot 313, the ridges 346 of the retention arm 322 interconnect with the corresponding ridges 348 of the slot 313, thereby locking the bite block 312 and the tongue suppressor 314 together.

It will be apparent that there is an almost infinite variety of other selectively mechanical adjusting and locking mechanisms that could exist between the bite block 12 and the tongue suppressor 14 which may be provided in accordance with the inventive principles set forth herein. It is intended, therefore, that the examples provided herein be viewed as exemplary of the principles of the present invention, and not as restrictive to particular structures for implementing those principles.

Unlike prior art devices, the present invention provides a tongue suppressing bite block having a novel structural design capable of maintaining the mouth of a patient in an open position while retaining the patient's tongue in the lower region of the mouth to avoid obfuscating the limited available work area within the patient's mouth. Additionally, the present invention is formed of a disposable material, thus avoiding the disadvantages and costs associated with having to clean and sterilize dental implements. The present invention also facilitates conducting dental procedures by improving visibility in and around the work area within a patient's mouth. In particular, the tongue suppressing bite block of the present invention bite has a simple, non-bulky design that does not require structural appendages protruding from the mouth of the patient which ultimately tend to interfere with the dentist performing the dental procedure and cause discomfort to the patient. Consistent with the foregoing, the present invention has a size and shape sufficient for being introduced into either side of the patient's mouth, thereby eliminating the need for a dentist to stock various sizes (e.g., small, medium and large) in order to accommodate different dental arch configurations. Moreover, the present invention is simple in construction and efficient in operation.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A dental apparatus adapted to be introduced into a mouth for suppressing a tongue and engaging teeth of a patient, the apparatus comprising:
   a deformable bite block having upper and lower engagement surfaces for engaging said patient's upper and lower teeth on a first side of the mouth;
   a tongue suppressor comprising a retaining arm extending from the bite block a distance selected to traverse and retain said tongue therebelow; and
   said tongue suppressor further comprising a flange, substantially perpendicular to the retaining arm and extending downward proximate a second side of the mouth.

2. The dental apparatus as defined in claim 1, wherein said bite block is provided with a slot for receiving therein said retaining arm and said retaining arm is slidably engaged within said slot.

3. The dental apparatus as defined in claim 2, wherein said retaining arm is retained in said slot by a retention mechanism.

4. The dental apparatus as defined in claim 3, wherein said retention mechanism is selected from the group consisting of a friction fit, a mechanical lock and a combination thereof.

5. The dental apparatus as defined in claim 1, wherein said bite block comprises a resilient engagement surface.

6. The dental apparatus as defined in claim 5, wherein said engagement surface is textured.

7. The dental apparatus as defined in claim 1, wherein said retaining arm is configured to correspond to retaining said patient's tongue toward one side of said patient's mouth.

8. The dental apparatus as defined in claim 1, wherein said bite block is angled to match a desired opening angle of said mouth.

9. The dental apparatus as defined in claim 1, further comprising a surface curved to conform to said mouth.

10. The dental apparatus as defined in claim 1, wherein said bite block and said tongue suppressor are pre-sterilized.

11. The dental apparatus as defined in claim 1, wherein said bite block is formed of a material selected to be disposable after a single use.

12. The dental apparatus as defined in claim 1, wherein said tongue suppressor is formed of a material selected to be disposable after a single use.

13. The dental apparatus as defined in claim 1, wherein said flange is configured to have a notch for cooperation with an aspiration device.

14. The dental apparatus as defined in claim 1, further comprising an emergency extraction mechanism.

15. The dental apparatus as defined in claim 14, wherein said emergency extraction mechanism comprises a tether secured to a portion of said retaining arm.

16. The dental apparatus as defined in claim 1, wherein said bite block and said tongue suppressor are configured to fit entirely within said patient's mouth.

17. The dental apparatus as defined in claim 1, further formed of a material comprising a flavoring.

18. A dental apparatus for suppressing a tongue and engaging teeth of a patient, the apparatus comprising:
   a deformable bite block having upper and lower engagement surfaces for engaging the upper and lower teeth proximate a first side of the mouth of a patient;
   a tongue suppressor comprising a retaining arm extending from the bite block a distance effective to retain said tongue proximate the inferior portion of the mouth;
   said tongue suppressor further comprising a flange extending substantially perpendicular to the retaining arm and extending downwardly into the inferior portion of, and proximate a second side of the mouth; and
   said bite block being provided with a slot, for receiving therein the retaining arm.

19. The dental apparatus as defined in claim 18, wherein said retaining arm is retained in said slot by a retention mechanism selected from the group consisting of a friction fit, a mechanical lock, and a combination thereof.

20. The dental apparatus as defined in claim 18, wherein said bite block and said tongue suppressor are pre-sterilized and disposable.

21. The dental apparatus as defined in claim 18, wherein said bite block and said tongue suppressor are configured to fit entirely within said patient's mouth.

22. The dental apparatus as defined in claim 18, further formed of a material comprising a flavoring.

* * * * *